United States Patent
Tsuji et al.

(10) Patent No.: US 8,771,931 B2
(45) Date of Patent: Jul. 8, 2014

(54) PERFUSION CULTURE METHOD AND PERFUSION CULTURE DEVICE FOR ORGAN OR TISSUE

(75) Inventors: Takashi Tsuji, Tokyo (JP); Kazuhisa Nakao, Tokyo (JP)

(73) Assignee: Organ Technologies, Inc., Tokyo (JP)

( * ) Notice: Subject to any disclaimer, the term of this patent is extended or adjusted under 35 U.S.C. 154(b) by 0 days.

(21) Appl. No.: 13/574,855

(22) PCT Filed: Jan. 25, 2011

(86) PCT No.: PCT/JP2011/051317
§ 371 (c)(1),
(2), (4) Date: Oct. 4, 2012

(87) PCT Pub. No.: WO2011/093268
PCT Pub. Date: Aug. 4, 2011

(65) Prior Publication Data
US 2013/0017533 A1    Jan. 17, 2013

(30) Foreign Application Priority Data
Jan. 29, 2010    (JP) ................... 2010-018938

(51) Int. Cl.
*A01N 1/00*      (2006.01)
(52) U.S. Cl.
USPC ............................. 435/1.2; 435/1.1
(58) Field of Classification Search
USPC .................................... 435/1.1, 1.2
See application file for complete search history.

(56) References Cited

U.S. PATENT DOCUMENTS 6,642,045 B1 * 11/2003 Brasile ................. 435/284.1

FOREIGN PATENT DOCUMENTS

| | | |
|---|---|---|
| JP | 11-164684 A | 6/1999 |
| JP | 2003-206201 | 7/2003 |
| JP | 2004-075583 | 3/2004 |
| WO | 99/15011 | 4/1999 |
| WO | 2004/101758 A1 | 11/2004 |

OTHER PUBLICATIONS

Naruse et al., Development of a new extracorporeal whole-liver perfusion system. Journal of Artificial Organs, vol. 6 (2003) pp. 211-217.*
Starzl et al., Refinements in the surgical technique of liver transplantation. Seminars in Liver Disease, vol. 5 No. 4 (Nov. 1985) pp. 349-356.*
Moers et al., Machine perfusion or cold storage in deceased-donor kidney transplantation. The New England Journal of Medicine, vol. 360 No. 1 (Jan. 1, 2009) pp. 7-19.*

(Continued)

*Primary Examiner* — Jon P Weber
*Assistant Examiner* — Kara Johnson
(74) *Attorney, Agent, or Firm* — Honigman Miller Schwartz and Cohn LLP; Cynthia M. Bott; Johnathan P. O'Brien

(57) ABSTRACT

Disclosed are a perfusion culture method and a perfusion culture device whereby a perfusate can be delivered to all parts of an organ or tissue so that the organ or tissue can be preserved while sufficiently maintaining the function thereof. Specifically disclosed is a method for perfusion culture of an organ or tissue removed from a mammal, said organ or tissue having been removed together with a second organ or tissue connected to the aforesaid organ or tissue in vivo, which comprises a step for fixing said second organ or tissue so as to hang the aforesaid organ or tissue and a step for perfusing blood vessels in the aforesaid organ or tissue with a perfusate.

8 Claims, 10 Drawing Sheets

(56) References Cited

OTHER PUBLICATIONS

Starzl et al., A flexible procedure for multiple cadaveric organ procurement. Surgery, Gynecology & Obstetrics, vol. 158 No. 3 (Mar. 1984) pp. 223-230.*

Wolthius et al., "Deceased donor retrieval." in MacPhee et al., Handbook of Renal and Pancreatic Transplantation (Hoboken, NJ, Wiley 2012), pp. 91-107.*

Butler A. J. et al. "Successful Extracorporeal Porcine Liver Perfusion for 72 HR1", Transplantation, 2002, pp. 1212-1218, vol. 73, No. 8.

Eventov-Friedman S. et al. "Embryonic pig liver, pancreas, and lung as a source for transplantation: optimal organogenesis without teratoma depends on distinct time windows", Proc. Natl. Acad. Sci. USA., 2005, pp. 2928-2933, vol. 102, No. 8.

Lechler R. I. et al. "Organ transplantation—how much of the promise has been realized?" Nature Medicine, 2005, pp. 605-613, vol. 11, No. 6.

Malchesky P. S., "The Spread and Breadth of Artificial Organ Technologies", Artificial Organs, 2006, pp. 655-656, vol. 30, No. 9.

Moers C. et al. "Machine Perfusion or Cold Storage in Deceased-Donor Kidney Transplantation", New England Journal of Medicine, 2009, pp. 7-19, vol. 360, No. 1.

Nui A. et al. "Successful ex vivo normothermic liver perfusion with purely artificial products using artificial blood", International Journal of Artificial Organs, 2003, pp. 46-52, vol. 26, No. 1.

Yang Y. G. et al. "Xenotransplantation: current status and a perspective on the future", Nature Reviews Immunology 2007, pp. 519-531, vol. 7.

English Translation of PCT/JP2011/051317 International Search Report, Mar. 1, 2011.

* cited by examiner

20

30

40

- Conventional stationary fixation
- Hanging fixation in solution

PERFUSION CULTURE METHOD AND PERFUSION CULTURE DEVICE FOR ORGAN OR TISSUE

CROSS-REFERENCE TO RELATED APPLICATIONS

This application is a National Phase application of PCT/JP2011/051317 filed Jan. 25, 2011, and claims priority to Japanese Application Serial No. 2010-018938 filed Jan. 29, 2010, the entire contents of which are hereby incorporated herein by reference.

TECHNICAL FIELD

The present invention relates to a perfusion culture method and perfusion culture device for long-term preservation of an organ or tissue that is removed primarily for the purpose of transplantation.

BACKGROUND ART

Organ transplantation is currently performed as the main therapy for irreversible dysfunction of organs due to illness or accidents. Although the number of transplantation cases has increased and their success rates have dramatically risen due to advance in immunosuppressive drug and transplantation technology, chronic shortage of organs has come to be a serious problem in transplantation medicine (Non-Patent Document 1). Although a method of transplanting organs from transplantation animals or development of genetically modified animals which are less likely to produce immunological rejection (Non-Patent Documents 2 and 3), as well as development of artificial organs which aims to replace an organ function with an artificial material (Non-Patent Document 4) are being carried out in order to overcome this organ shortage, none of the technological developments have yet to replace the functions of adult organs.

Major reasons for shortage of donor organs supplied for transplantation are not only the number of organs provided, but also the short period of time that the removed organ can be preserved in a transplantable state. For this reason, development of technology to preserve the removed organ ex vivo in a transplantable state for a long time is being promoted. The most widely employed method today is cold storage of replacing blood within the organ with a low-temperature organ preservation solution to suppress cell metabolism, and then immersing it in a low-temperature preservation solution. There is also a cold perfusion method of immersion preservation at a low temperature while perfusing the vascular network within the organ with a low-temperature organ preservation solution, the purpose of which is removing the waste product within the preserved organ. Trials for this are recently being carried out in Europe and the United States (Non-Patent Document 5). However, there is a limit to the period of time which organs preserved with these methods can be safely used (for example, the limit of use for liver by cold storage is thought to be 20 hours), and a technology for further extending the preservation period is in need.

As a device for long-term preservation of liver, an artificial organ system is proposed, wherein an organ hanging tube is inserted into the inferior vena cava stump of the liver, the entire liver is hanged, and the liver is supported by said hanger tube and the surface of a container part the liver is placed upon, which may allow it to be kept in a dilated state (See, e.g., paragraph [0024] of Patent Document 1, FIG. 2, and FIG. 4).

RELATED ART

Patent Document 1: Japanese Unexamined Patent Application Publication No. 2003-206201
Non-Patent Document 1: Lechler R I. et al.: Nat. Med. 11 (6): 605, 2005
Non-Patent Document 2: Eventov-Friedman S. et al.: Proc. Natl. Acad. Sci. USA. 102 (8): 2928, 2005
Non-Patent Document 3: Yang Y G. et al.: Nat. Rev. Immunol. 7 (7): 519, 2007
Non-Patent Document 4: Malchesky P S. et al.: Artif. Organs. 30 (9): 655, 2006
Non-Patent Document 5: Moers C. et al.: N. Engl. J. Med. 360 (1): 7, 2009
Non-Patent Document 6: Butler A J. Et al.: Transplantation 73 (8): 1212, 2002
Non-Patent Document 7: Nui A. et al.: Int. J. Artif. Ogans 26 (1): 46, 2003

DISCLOSURE OF THE INVENTION

Problems to be Solved by the Invention

In the method of Patent Document 1, the organ is easily damaged since a hanger tube is inserted into the organ. Moreover, the present inventors have confirmed in an experiment using a similar configuration that the perfusate is not delivered to all parts of the liver.

Accordingly, the object of the present invention is to provide a perfusion culture method and perfusion culture device, wherein an organ can be preserved for a long time while sufficiently maintaining the function thereof by delivering a perfusate to all parts of the organ.

Means for Solving the Problems

As a result of repeated investigations to solve the above problems, the present inventors have found that in perfusion culture of an organ or tissue (hereinafter sometimes referred to as "organ etc."), rather than hanging the organ etc. itself, by removing the organ etc. along with a second organ or tissue which is connected to the organ etc. in vivo, and hanging the organ etc. to be cultured by fixing the aforementioned second organ or tissue, culturing can be performed so that the perfusate is delivered to all parts without causing damage to the organ etc.

Further, it was found that when hanging and culturing the organ etc., by immersing it in an organ etc. immersion liquid so that at least a part of the organ etc. receives buoyancy, the perfusate can be delivered to more parts of the organ etc. and the period of time the function thereof can be maintained is significantly extended, and thus the present invention was completed.

In other words, one aspect of the present invention relates to:

[1] A method for perfusion culture of an organ or tissue removed from a mammal, wherein said organ or tissue is removed together with a second organ or tissue which is connected to the aforesaid organ or tissue in vivo, comprising a step of hanging the aforesaid organ or tissue by fixing said second organ or tissue, and a step of perfusing the blood vessels in the aforesaid organ or tissue with a perfusate;

[2] The perfusion culture method according to the above [1], wherein in the said perfusion step, at least a part of the aforesaid organ or tissue is immersed in an organ etc. immersion liquid;

[3-1] The perfusion culture method according to the above [1] or [2], wherein the aforesaid organ or tissue is the liver, and said second organ or tissue is the diaphragm;

[3-2] The perfusion culture method according to the above [1] or [2], wherein the aforesaid organ or tissue is the liver, and said second organ or tissue are the diaphragm and the rib;

[4] The perfusion culture method according to the above [1] or [2], wherein the aforesaid organ or tissue is the kidney, and said second organ or tissue is adipose tissue surrounding the kidney; and

[5] A method for perfusion culture of an organ or tissue removed from a mammal, comprising a step of hanging the aforesaid organ or tissue, and immersing at least a part of aforesaid organ or tissue in an organ etc. immersion liquid, and a step of perfusing the blood vessels in the aforesaid organ or tissue with a perfusate.

In other words, another aspect of the present invention relates to:

[6] A perfusion culture device for an organ or tissue, comprising a suspension means for hanging the organ or tissue, a perfusate inflow cannula for allowing a perfusate to flow into the aforesaid organ or tissue, and a perfusate outflow cannula for allowing the perfusate to flow out from the aforesaid organ or tissue;

[7] The perfusion culture device according to the above [6], further comprising a vessel that can allow immersion of at least a part of said organ or tissue in the organ etc. immersion liquid while the aforesaid organ or tissue is being hanged;

[8-1] The perfusion culture device according to the above [6] or [7], wherein the aforesaid organ or tissue is the liver, and further comprising a biliary cannula for recovering bile;

[8-2] The perfusion culture device according to the above [6], [7] or [8-1], wherein the aforesaid organ or tissue is the liver, and the said suspension means has a configuration where the liver removed together with the rib and the diaphragm from a mammal is fixable at the rib;

[9-1] The perfusion culture device according to the above [6] or [7], wherein the aforesaid organ or tissue is the kidney, and further comprising a ureteral cannula for recovering urine; and

[9-2] The perfusion culture device according to the above [6], [7] or [9-1], wherein the aforesaid organ or tissue is the kidney, and the said suspension means has a configuration where the kidney removed together with the surrounding adipose tissue from a mammal is fixable at the adipose tissue.

Advantage of the Invention

According to the perfusion culture method and perfusion culture device for organ or tissue of the present invention, since the perfusate can be delivered to all parts of the organ without causing damage to the organ, it can be preserved for a long time while maintaining organ function to be provided for transplantation in a good state.

DESCRIPTION OF EMBODIMENTS

Figure 1:
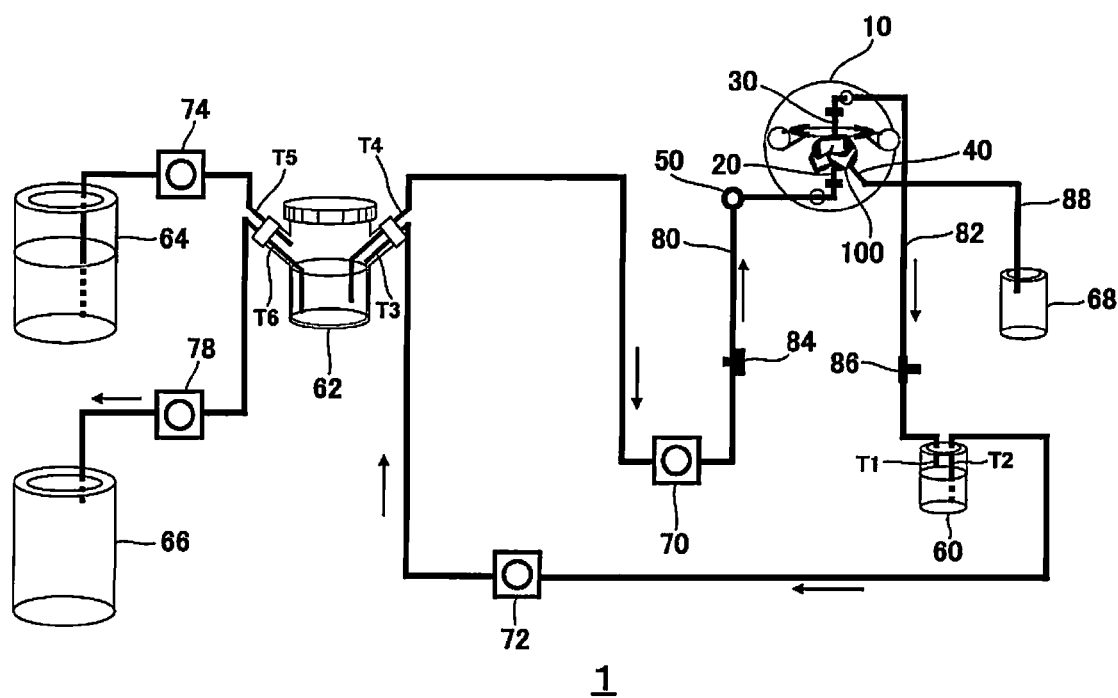
FIG. 1 is a schematic diagram showing an example of the perfusion culture device for an organ or tissue according to the present invention.

Perfusion Culture Method for Organ or Tissue

The first aspect of the organ perfusion culture method according to the present invention is a method for perfusion culture of an organ or tissue removed from a mammal, characterized in that the aforementioned organ or tissue is removed together with a second organ or tissue which is connected to the aforesaid organ or tissue in vivo, comprising a step of hanging the organ or tissue by fixing the second organ or tissue, and a step of perfusing the blood vessels in the organ or tissue with a perfusate.

"Mammal" herein is not particularly limited, and the perfusion culture method according to the present invention can be utilized for organ etc. of any mammal. When the organ etc. cultured with the method according to the present invention is employed for transplantation, the mammal can be appropriately selected according to the subject to which the organ etc. is transplanted (recipient), examples of which include humans, pigs, cows, monkeys, baboons, dogs, and cats. When the recipient is a human, the organ etc. used is primarily that removed from a brain-dead patient.

"Organ or tissue (organ etc.)" herein is not particularly limited as long as it is an organ or tissue suitable for perfusion culture, examples of which include the heart, liver, kidney, lung, pancreas, stomach, small intestine, large intestine, tooth and its surrounding tissue, and hair and its surrounding tissue.

"Perfusion culture" of organ etc. in the present invention refers to linking a tube such as a cannula to the blood vessels of a removed organ etc. and allowing the perfusate to flow in and out in a manner similar to blood flow in order to culture the organ. Those skilled in the art can appropriately select a well-known composition or a corresponding composition of the perfusate according to the type of mammal or organ. For example, it may be those comprising nutrients such as sugars or amino acids necessary for cell survival. A culture solution employed for general cell culture or an organ preservation solution employed for organ preservation can be employed, and the composition thereof is not particularly limited.

In the perfusion culture method according to the present invention, an organ etc. removed together with a second organ or tissue which is connected to the organ etc. in vivo is employed. According to such configuration, since the aforementioned second organ or tissue can be fixed in order to hang the organ etc. to be cultured, the culture solution can be delivered to all parts of the organ etc. without causing damage to the organ etc. to be cultured.

The second organ or tissue is preferably an organ or tissue which is connected to the organ etc. in vivo, more preferably an organ or tissue which is connected to the upper part of the organ etc. in vivo. By hanging with such organ or tissue, the organ etc. can be cultured in an environment similar to the in vivo configuration. An environment similar to the in vivo configuration herein means an environment where the organ etc. can maintain its natural shape without being subjected to compression from hard materials such as the inner surface of a container. Because the conventional perfusion culture for organ etc. was carried out by placing the organ etc. in a container such as a petri dish, the blood vessels in the portion in contact with the petri dish was compressed, and the perfusate was not sufficiently delivered. According to the method of the present invention, since the organ etc. is hanged and cultured in an environment similar to the in vivo configuration, the perfusate can be delivered to all parts of the organ etc.

Further, when fixing the second organ or tissue, since there is no inconvenience if the second organ or tissue is damaged, it can be firmly fixed with methods such as inserting a hanger tube, clipping with a clip, or sewing with a suture.

For example, if the organ to be cultured is the liver, the diaphragm is connected to the upper part thereof in vivo, and the aforementioned diaphragm is connected to the rib. Accordingly, only the diaphragm, or the diaphragm and the rib can be employed as the second organ(s) or tissue(s). When removing the liver from a mammal, if the diaphragm is removed together, the liver can be hanged in an environment that approximates that in vivo by fixing the aforementioned diaphragm. If the rib in addition to the diaphragm is removed together, the rib can be fixed to allow a more stable hanging.

Other examples of the second organ or tissue include, but is not limited to: for culturing the kidney or pancreas, adipose tissue attached to the surface of the kidney or pancreas; for culturing an organ of the digestive system, an upstream adjacent organ (specifically, the stomach or duodenum for culturing the small intestine and the small intestine for culturing the large intestine); for culturing the tooth and its surrounding tissue, the jaw bone, alveolar bone, root bone, and gingiva; and for culturing the hair and its surrounding tissue, the epidermis, dermis, and adipose tissue.

In the perfusion culture method of the present invention, the step of perfusing the blood vessels in the organ etc. with a perfusate (perfusion step) can be performed by, for example, linking a tube connected to the blood vessels of the organ etc. to a pump, and allowing the perfusate to flow in and out.

The perfusion culture method of the present invention is preferably carried out by immersing at least a part of the organ etc. in the organ etc. immersion liquid in the perfusion step. By doing so, at least a part of the organ etc. receives buoyancy, and therefore an environment that further approximates the in vivo configuration can be created compared to simple hanging, and the perfusate can be delivered to all parts of the organ etc. A state where at least 30% of the organ etc. exists in the liquid is preferred, more preferably 50%, further preferably 80%, and most preferably, the entire organ etc. exists in the liquid. As with the perfusate, those skilled in the art can appropriately select the organ etc. immersion liquid according to the type of mammal and organ etc., and it may be of the same or a different composition as the perfusate.

The second aspect of the perfusion culture method for organ or tissue according to the present invention is a method for perfusion culture of an organ etc. removed from a mammal, characterized in that it comprises a step of hanging the organ etc. and immersing at least a part of the organ etc. in an organ immersion liquid, and a step of perfusing the blood vessels in the organ etc. with a perfusate.

The terms used in the first aspect of the perfusion culture method for organ or tissue according to the present invention are employed synonymously in the second aspect, and description therefore is omitted here.

In the second aspect of the method according to the present invention, the step of hanging the organ etc. can be any method as long as the organ etc. can maintain the function thereof, although it is preferably a state similar to the environment in vivo. Accordingly, it is preferred to hang in the same vertical orientation as in vivo using a method as non-invasive as possible.

Perfusion Culture Device for Organ or Tissue

The perfusion culture device for an organ or tissue according to the present invention is characterized in that it comprises a suspension means for hanging the organ etc., a vessel that can allow immersion of at least a part of said organ etc. in an organ etc. immersion liquid while the organ etc. is being hanged, a perfusate inflow cannula for allowing a perfusate to flow into the organ etc., and a perfusate outflow cannula for allowing the perfusate to flow out from the organ etc.

When employing the aforementioned device for culturing the liver, it is preferred to further comprise a biliary cannula. By inserting a biliary cannula into the bile duct of the liver, the bile secreted from the liver can be recovered on the outside of the culture vessel.

When employing the aforementioned device for culturing the kidney, it is preferred to further comprise a ureteral cannula. By inserting a ureteral cannula into the urinary duct of the kidney, the urine secreted from the kidney can be recovered on the outside of the culture vessel.

Moreover, when employing the aforementioned device for culturing the liver, wherein the liver is removed together with the rib and the diaphragm, the suspension means preferably has a configuration that can fix the rib.

Moreover, when employing the aforementioned device for culturing the kidney, wherein the kidney is removed together with the surrounding adipose tissue, the suspension means preferably has a configuration that can fix the adipose tissue.

As an example the perfusion culture device according to the present invention, a liver culturing device 1 is shown in FIG. 1, and its overview will be described below. The liver culturing device 1 is for culturing the liver removed together with the diaphragm and rib, and the liver is subjected to perfusion culture in a state where the entire liver is immersed in the liquid.

The liver culturing device 1 comprises a liver fixation culture vessel 10, as well as a perfusate inflow cannula 20 and a perfusate outflow cannula 30 which will be fixed to the liver, and tubes 80 and 82 are connect to each cannula. The tube 80 which will be linked to the perfusate inflow cannula 20 is connected to a microcarrier spinner flask 62 via a perfusate inflow peristaltic pump 70, and supplies the perfusate within the microcarrier spinner flask 62 to the perfusate inflow cannula 20.

The perfusate that flowed into the liver 100 through the perfusate inflow cannula 20 will flow out to the perfusate outflow cannula 30, and exported into the microcarrier spinner flask 62 through tube 82 etc. linked to the perfusate outflow cannula 30.

Preferable examples of each constituent element will now be described.

Figure 2:
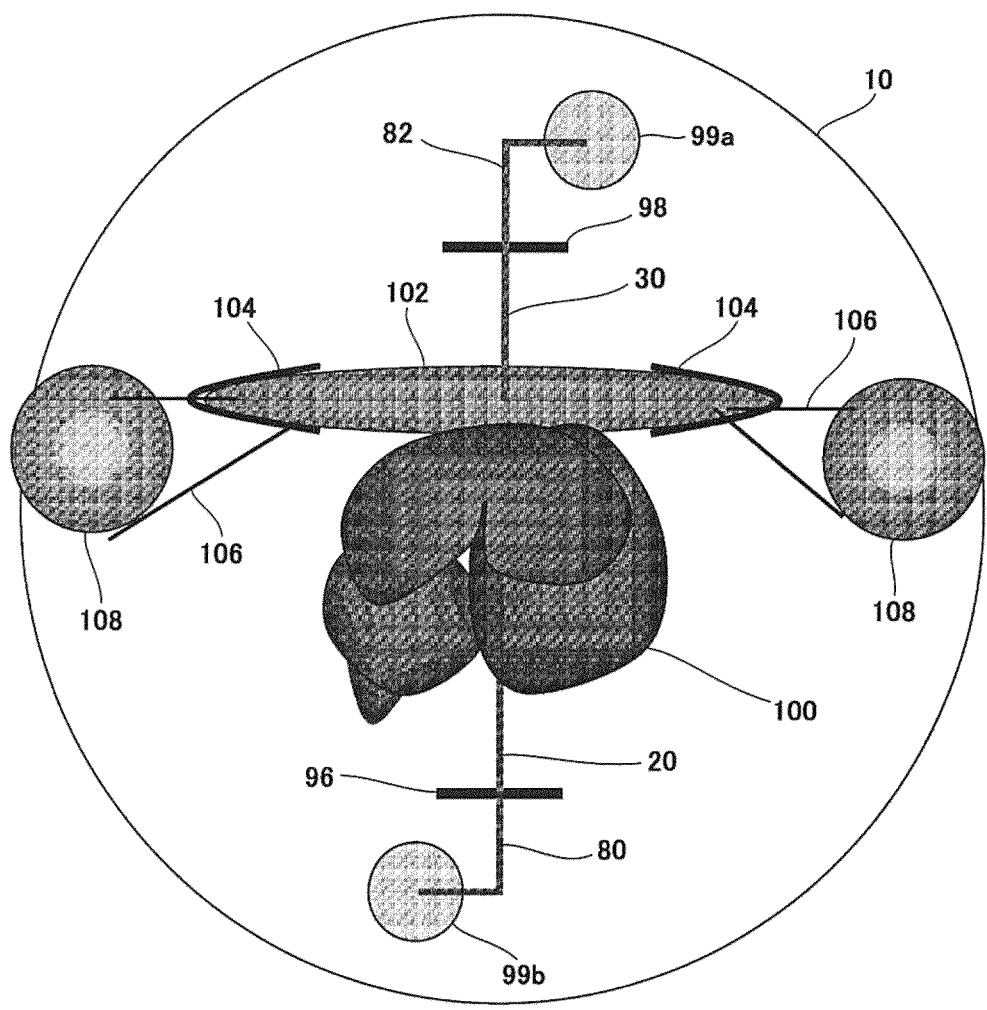
FIG. 2 is a schematic diagram of the magnified culture vessel of the perfusion culture device shown in FIG. 1. The liver is shown in the schematic diagram of FIG. 2 merely as an exemplification.

A magnification of the liver fixation culture vessel 10 is shown in FIG. 2.

Culture vessel 10 comprises suspension means 106 and 108 which allows the liver 100 to be hanged by the ribs 104. The interior of the culture vessel 10 has a configuration where the vessel can be filled with liquid, and the entire liver 100 is immersed so that it receives buoyancy. In addition, the wall of the culture vessel 10 has through-holes 99a and 99b formed thereon for passing the tubes 80 and 82 linked to the cannula.

The culture vessel 10 also comprises fixtures 96 and 98 for fixing the cannula or tube linked thereto. By fixing the cannula with the fixtures 96 and 98, the cannula is prevented from being inserted too far into the organ and causing damage thereto or from being detached from the organ, so that the culture solution can be stably circulated. For fixtures 96 and 98, for example, a column-shaped member having a slit of a few millimeters at the tip into which the cannula or tube is fittable can be employed. The cannula is fixed by anchoring the aforementioned member to the inner wall of the culture vessel and fitting the cannula into the slit.

The culture vessel 10 may be of any material, and can be fabricated with e.g. glass or acrylic.

Figure 3:
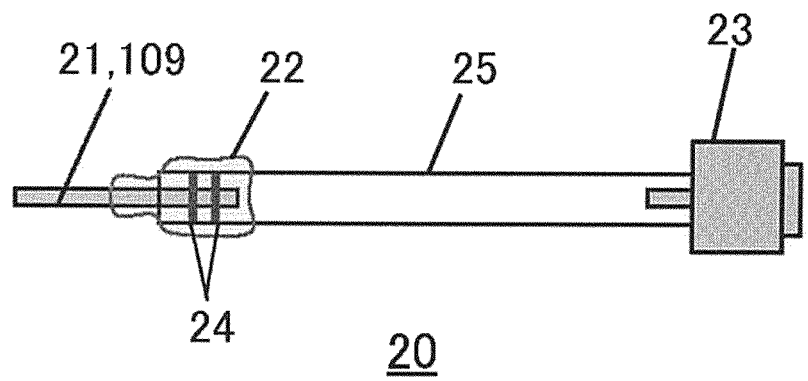
FIG. 3 is a schematic diagram showing an example of the cannula to be connected to the organ or tissue according to the present invention.
Figure 3:
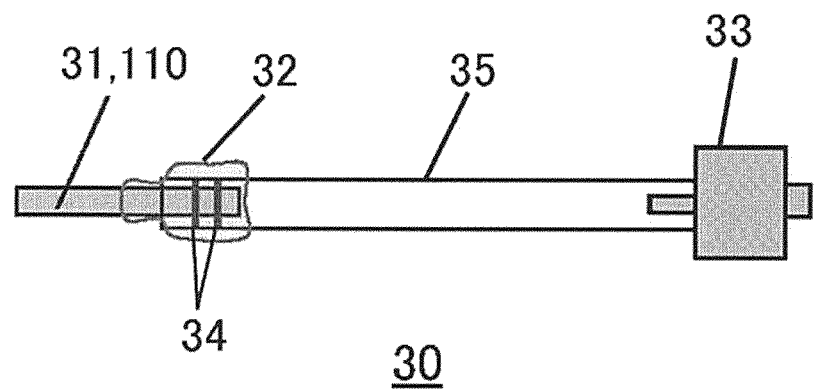
Figure 3:
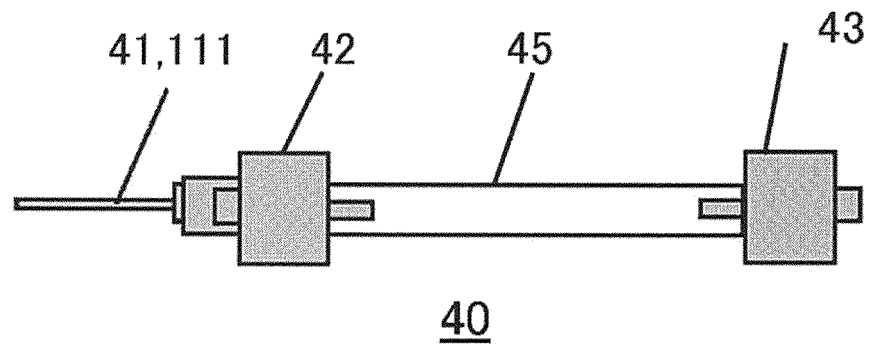

The perfusate inflow cannula 20 is shown in FIG. 3 top column, the perfusate outflow cannula 30 in FIG. 3 middle column, and the biliary cannula 40 in FIG. 3 bottom column. In each cannula shown in FIG. 3, the size etc. of each member, for example the catheter part configuring the cannula can be altered depending on the organ or tissue applied. For example, in liver perfusion culture, the perfusate inflow/outflow cannula is fabricated by cutting off catheter parts 21 and 31 of indwelling needles (e.g. 22G for inflow and 16G for outflow), connecting them to silicone tubes 25 and 35 (e.g. ID 1 mm), sewing and fixing them at two positions with flexible silk sutures 24 and 34, and wrapping Parafilms 22 and 32. The biliary cannula 40 is fabricated by connecting catheter part 41 of the indwelling needle (e.g. 27G) to silicone tube 45 (e.g. ID 1 mm) via a luer lock fitting 42 (e.g. for 1.5 mm ID). Luer lock fittings 23, 33, and 43 are connected to ends opposite from the catheter on each cannula so that they can be linked to tubes 80, 82, and 88 (FIG. 1).

The perfusate inflow cannula 20 and the perfusate outflow cannula 30 are each directly or indirectly connected to e.g. the portal vein of the liver 100 and the vein of the liver, respectively.

The perfusate inflow cannula 20 is connected to the perfusate inflow peristaltic pump 70, and the perfusate flows from the perfusate inflow cannula 20 into the liver 100 by operating the pump 70. The perfusate that flowed in passes through the liver 100 and flows out from the perfusate outflow cannula 30, and flows into the tube 82. In addition, the bile secreted from the liver is recovered from the biliary cannula 40 into the bile recovery circuit (bile recovery tube 88 and bile recovery bottle 68).

The perfusate inflow cannula 20 is linked to the silicone tube 80 (e.g. ID 2 mm) with luer lock fitting 23 (e.g. for 2.5 mm ID), and the silicone tube is similarly connected to a Pharmed tube (e.g. ID 3.15 mm) with a luer lock fitting. Fluorine grease is applied to this Pharmed tube, and set up on the perfusate inflow peristaltic pump 70.

The perfusate outflow cannula 30 is linked to the silicone tube 82 (e.g. ID 2 mm) with luer lock fitting 33 (e.g. for 2.5 mm ID). This silicone tube is further connected to Teflon tube T1 of a Scott bottle with a silicone stopper 60 (e.g. 100 ml) having three Teflon tubes (e.g. ID 1 mm; T1 and T2, the third tube is not shown) pierced through on the lid.

On the other hand, to one of the remaining two Teflon tubes of the Scott bottle 60, a silicone tube (e.g. ID 2 mm) long enough to reach the bottom of the bottle is connected on the inside (T2 in FIG. 1), and a Pharmed tube having silicone tubes (e.g. ID 2 mm) linked on both sides is connected on the outside. The other end of the silicone tube is connected via the perfusate outflow peristaltic pump 72 to Teflon tube T3 (ASONE), which does not have a silicone tube linked on the inside of the bottle and the tip does not reach the liquid surface, among the three Teflon tubes (T3 and T4, the third tube is not shown) pierced through the right lid of the microcarrier spinner flask with a silicone stopper (e.g. 1000 ml) 62 in the Figure.

The third Teflon tube pierced through the lid of the Scott bottle 60 has an air filter connected on the outside of the bottle.

The perfusate is kept warm by a heater wrapped around the microcarrier spinner flask 62. The temperature is preferably the average body temperature of the target mammal, and in case of humans at around 37° C. The heater employed is preferably CELLMASTER Flexible Heater (Wakenyaku, Kyoto, Japan) and CELLMASTER 1700 (Wakenyaku), Temperature Electrode (Mettler Toled, Tokyo, Japan). The two lids of the microcarrier spinner flask 62 each have three Teflon tubes pierced through. Teflon tube T4 linked to a silicone tube (e.g. ID 2 mm) pierced through the right lid in the Figure that reaches the bottom of the bottle is linked to the perfusate inflow peristaltic pump 70 via a silicone tube.

The other Teflon tube pierced through the right lid in the Figure has an air filter connected on the outside of the bottle.

When culturing the organ etc. at a low temperature, a well-known cooling device can be employed instead of the heater to cool the perfusate. The cooling temperature is preferably 4° C. to 35° C., more preferably 20° C. to 35° C. Moreover, when culturing the organ etc. at a low temperature, it is preferred that the liquid for immersing the organ etc. is also at a low temperature, and the organ etc. in culture is simultaneously cooled. Examples of cooling devices employed for such cooling include various radiators and Peltier cooling device.

Flow path switch cocks 84 and 86 are installed on the silicone tubes between the perfusate inflow peristaltic pump 70 and the perfusate inflow cannula 20, and between the perfusate outflow cannula 30 and the Scott bottle 60, and a perfusate recovery tube (e.g. 15 ml) for collecting the perfusate is set up on these.

Figure 4:
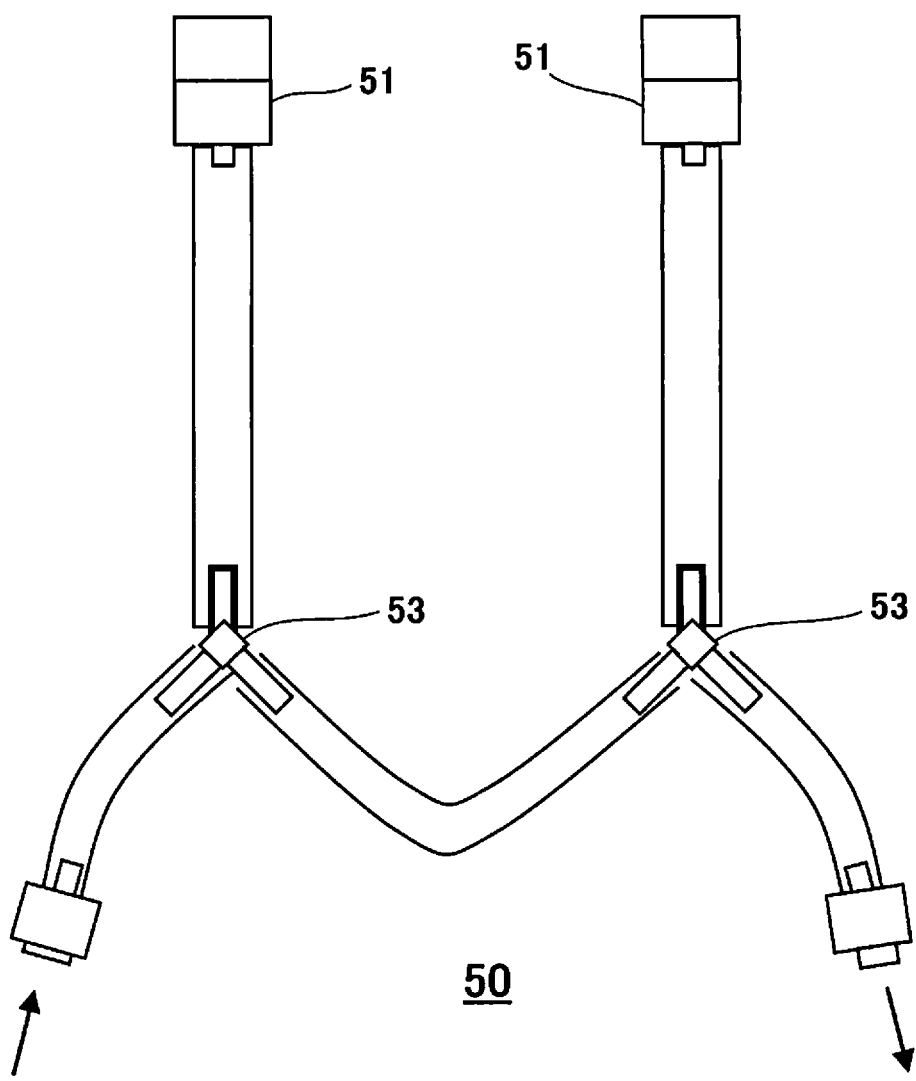
FIG. 4 is a schematic diagram showing an example of the bubble removal device.

A bubble removal device 50 is installed between the perfusate inflow peristaltic pump 70 and the perfusate inflow cannula 20. The configuration of the bubble removal device 50 is shown in FIG. 4. Silicone tubes stopped with luer lock fitting plugs 51 are linked with Y-shaped tubes to prevent bubbles entrained in the circuit from flowing into the liver, and at the same time a device for eliminating these bubbles from the luer lock fitting plugs 51 (ISIS) is installed. Mini-fittings (F) 53 (for 6.5 mm ID; ISIS) are preferably employed as the Y-shaped tubes.

In order to exchange the perfusate every 24 hours of perfusion culture, among three Teflon tubes (T5 and T6, the third tube is not shown) pierced through the left lid of the microcarrier spinner flask 62 in the Figure as shown in FIG. 1, to each of Teflon tube T5 which does not have a silicone tube linked on the inside and the tip does not reach the liquid surface, and Teflon tube T6 which has a silicone tube linked on the inside and the tip reaches the liquid surface, are connected a Pharmed tube having silicone tubes connected on both ends. An air filter is connected to the remaining Teflon tube.

The silicone tube connected to Teflon tube T5 is linked to a perfusate addition Scott bottle 64 (e.g. 2000 ml) comprising fresh media via a perfusate addition peristaltic pump 74.

The silicone tube connected to Teflon tube T6 is linked to a perfusate recovery Scott bottle 66 (e.g. 2000 ml) via a perfusate recovery peristaltic pump 78.

Figure 5:
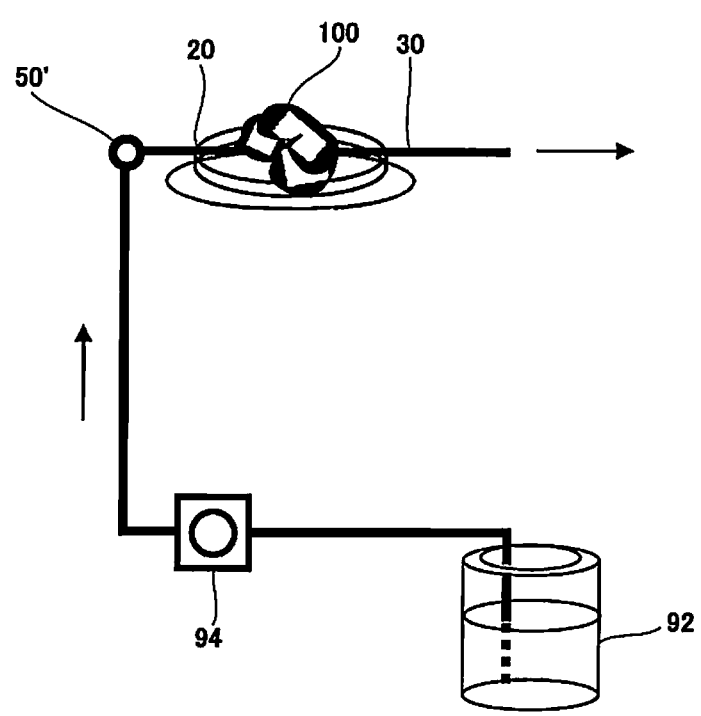
FIG. 5 is a schematic diagram showing an example of the preperfusion circuit.

The preperfusion circuit shown in FIG. 5 is constructed so that the perfusate can be pumped during removal of the liver.

The perfusate inflow cannula 20 is linked to a silicone tube (e.g. ID 2 mm) with luer lock fitting 23, and this silicone tube is connected to a bubble removal device 50'. Another silicone tube is linked to the bubble removal device 50', a Pharmed tube (e.g. ID 3 mm) applied with fluorine grease is further linked to the silicone tube, and the Pharmed tube is set up on the peristaltic pump 94. A silicone tube (e.g. ID 2 mm) is linked to the other end of the Pharmed tube to pump the perfusate from a Scott bottle 92.

This resulted in the perfusate pumped from the Scott bottle 92 to flow into the liver through the perfusate inflow cannula 20 and flow out to the perfusate outflow cannula 30. The perfusate outflow cannula 30 is linked to a silicone tube (e.g. ID 2 mm) with luer lock fitting 33, and the perfusate which flowed out of the liver is exported from the silicone tube and disposed.

The liver connected to the preperfusion circuit can be connected to the perfusion circuit shown in FIG. 1 by disconnecting the perfusate inflow cannula 20 and the perfusate outflow cannula 30 from the silicone tubes by luer lock fittings 23 and 33, and then connecting the luer lock fittings 23 and 33 to the luer lock fittings of the silicone tubes 80 and 82 (FIG. 1).

Although the overview of the liver culturing device 1 has been described as an example the perfusion culture device according to the present invention, other organ etc. can also be perfusion cultured with a configuration similar to the liver culturing device 1. For example, the kidney can be perfusion cultured with a similar configuration. In such a case, the configuration can be altered as described below.

For example, the cannula are similar those employed for liver perfusion culture shown in FIG. 3, except that catheter parts 109 and 110 of indwelling needles (e.g. 26G for inflow and 16G for outflow) are used for the perfusate inflow/outflow cannula, and tip part 111 of a gel loading tip with a narrow tip (e.g. GELoader Tip 0.5-200 from Eppendorf) is used for the ureteral cannula.

In addition, the perfusate inflow cannula 20, the perfusate outflow cannula 30, and the ureteral cannula 40 are similar as in the case for the liver except that they are each directly or indirectly connected to for example the renal artery of the kidney, the renal vein of the kidney, and the urinary duct, respectively.

The perfusate inflow cannula 20 is linked to the silicone tube 80 (e.g. ID 1.0 mm) with luer lock fitting 23 (e.g. for 1.5 mm ID), and the silicone tube is similarly connected a Pharmedtube with a luer lock fitting. Fluorine grease is applied to this Pharmed tube (e.g. ID 1.6 mm), and set up on the perfusate inflow peristaltic pump 70.

The perfusate outflow cannula 30 is linked to the silicone tube 82 (e.g. ID 1 mm) with luer lock fitting 33 (e.g. for 1.5 mm ID). This silicone tube is further connected to Teflon tube T1 of the three Teflon tubes (e.g. ID 1 mm; T1 and T2, the third tube is not shown) pierced through the lid of the Scott bottle with a silicone stopper 60 (e.g. 100 ml).

On the other hand, to one of the remaining two Teflon tubes of the Scott bottle 60, a silicone tube (e.g. ID 2 mm) long enough to reach the bottom the bottle is connected on the inside (T2 in FIG. 1), and a Pharmed tube having silicone tubes (e.g. ID 2 mm) linked on both sides is connected on the outside. The other end of the silicone tube is connected via the perfusate outflow peristaltic pump 72 to Teflon tube T3 (ASONE) which does not have a silicone tube liked on the inside of the bottle and the tip does not reach the liquid surface, among the three Teflon tubes (T3 and T4, the third tube is not shown) pierced through the right lid of the microcarrier spinner flask with a silicone stopper (e.g. 1000 ml) 62 in the Figure.

The third Teflon tube pierced through the lid of the Scott bottle 60 is connected to an air filter on the outside of the bottle.

Moreover, the perfusate recovery tube, the bubble removal device, and the media exchange perfusion circuit can be used in a configuration similar to that for the liver culturing device.

The preperfusion circuit shown in FIG. 5 is constructed so that the perfusate can also be pumped during removal of the kidney. The perfusate inflow cannula 20 is linked to a silicone tube (e.g. ID 1.0 mm) with luer lock fitting 23, and this silicone tube is connected to the bubble removal device 50'. Another silicone tube is linked to the bubble removal device 50', a Pharmed tube (e.g. ID 1.6 mm) applied with fluorine grease is further linked, and set up on the peristaltic pump 94. A silicone tube (e.g. ID 1.0 mm) is linked to the other end of the Pharmed tube to pump the perfusate from the Scott bottle 92.

The perfusate thereby pumped from the Scott bottle 92 flows into the kidney through the perfusate inflow cannula 20 and flows out to the perfusate outflow cannula 30. The perfusate outflow cannula 30 is linked to a silicone tube (e.g. ID 2 mm) with luer lock fitting 33, and the perfusate which flowed out of the kidney is exported from the silicone tube and disposed. The kidney connected to the preperfusion circuit can be connected to the perfusion circuit shown in FIG. 1 by disconnecting the perfusate inflow cannula 20 from the silicone tube by luer lock fitting 23, and then connecting the luer lock fitting 23 to the luer lock fitting of the silicone tube 80 (FIG. 1).

The terms used herein are employed to describe particular embodiments, and not intended to limit the invention.

In addition, the term "comprising" and "including" as used herein intends, unless the context clearly indicates otherwise, that the stated items (parts, steps, elements, numbers etc.) exist, and does not exclude the existence of other items (parts, steps, elements, numbers etc.).

Unless otherwise defined, all terms used herein (including technical and scientific terms) have the same meaning as that broadly recognized by those skilled in the art of the technology to which the present invention belongs. The terms used here, unless explicitly defined otherwise, should be construed as having meanings consistent with the meanings herein and in the related technological field, and are not to be construed as idealized or excessively formal meanings.

The embodiments of the present invention may be described referring to schematic diagrams. In such a case, they may be exaggerated in presentation in order to clarify the description.

Terms such as first and second may be employed to express various elements, but it shall be recognized that these elements are not to be limited by these terms. These terms are employed to differentiate one element from the other element, and for example, it is possible, without departing from the scope of the invention, to describe the first element as the second element, and similarly to describe the second element as the first element.

The present invention will now be described in detail referring to Examples. However, the present invention can be embodied by various aspects, and shall not be construed as being limited to the Examples described herein.

EXAMPLES

The present invention will now be specifically described based on Examples, but shall not be limited to these in any way.

1. Preparation of Perfusate

The perfusate employed was L-15 medium (Sigma, Mo., US) supplemented with 10% FCS (Life Technologies, Calif., US) and antibiotics-antimycotics mixture solution (nacalai tesque, Japan), gentamicin sulfate (Wako, Osaka, Japan), L-Glutamine (Life Technologies). 1000 ml of the perfusate was placed in a 1000 ml microcarrier spinner flask (Bellco) with a silicone stopper, and kept warm at 37° C.

2. Removal of Liver and Connection to Preperfusion Circuit

The liver was removed from a rat, and connected to the preperfusion circuit shown in FIG. 5.

A desiccator was filled with diethyl ether (Wako), an 8-10 week-old Wistar rat (SLC) was transferred to the desiccator for inhalation anesthesia, and then 400 μl of pentobarbital sodium (TCI, Tokyo, Japan) solution at a final concentration of 25 mg/ml intraperitoneally injected with a 25G injection needle (Terumo) and a 1 ml syringe (Terumo).

Incision was made to the skin of a rat under deep anesthesia from lower abdomen to below the throat along the midline. The peritoneum was incised, and the organs of the digestive system were moved to expose the liver and the portal vein. The liver was lifted towards the rib to expose the hepatic artery, and silk suture No. 7 (Natume) was pulled through from under the hepatic artery and ligated. Similarly, silk suture No. 4 (Natume) was pulled through the subhepatic inferior vena cava to create one ligature loop. Silk suture No. 7 (Natume) was pulled through the splenogastric vein and ligated. Two bent silk suture No. 4 (Natume) were pulled through the portal vein with interval to create two ligature loops. The perfusate was flowed through the preperfusion circuit (FIG. 5) in advance at 10 ml/min, the portal vein was bisected at a site away from the liver than the two portal vein ligature loops, and the perfusate inflow cannula 20 was quickly inserted into the portal vein. The subhepatic inferior vena cava was immediately cut downstream from the ligature loop to allow inflow of the perfusate.

The two portal vein ligature loops were ligated to fix the cannula 20 to the portal vein, and the cannulation portion was fixed with a small amount of Aron Alpha A (Daiichi Sankyo, Tokyo, Japan). The common bile duct was bisected and the biliary cannula 40 was inserted, and then fixed with Aron Alpha A (Daiichi Sankyo). The diaphragm was exposed, and the left and right phrenic arteries/veins were ligated with silk suture No. 7 (Natume).

The diaphragm was cut out along with the rib by making incisions between the ribs, and the portion of the rib above the incision was cut open to below the throat. Incision was made to a part of the rib, silk suture No. 4 (Natume) was pulled through the suprahepatic inferior vena cava, and two ligature loops were created. The loops were ligated, the outflow of the perfusate from the subhepatic inferior vena cava was stopped, and the right atrium was bisected. The perfusate outflow cannula 30 was inserted into the bisected right atrium portion, the two ligature loops of suprahepatic inferior vena cava were ligated to fix the cannula, and the ligation and cannulation portions were fixed with Aron Alpha A. After removing the organs surrounding the liver and the connective tissue, the liver was cut away from backside with the rib and the diaphragm still attached to the liver.

3. Connection to Liver Perfusion Circuit 3-1. Stationary Fixation (Conventional Method)

First, while still connected to the preperfusion circuit, the perfusate inflow cannula 20 was fixed to the fixture 96 of the culture vessel 10, the perfusate outflow cannula 30 was fixed to the fixture 98, and the biliary cannula 40 was also fixed to a fixture (not shown). The biliary cannula 40 was connected via luer lock fitting 43 (ISIS) to the bile recovery circuit that flows to the outside of the culture vessel 10 (tube 88 and Scott bottle 68).

Next, the silicone tube (ASONE) connected to the perfusate inflow cannula 20 was clipped with Pean hemostatic forceps (Natume) to temporarily stop the liquid flow, and then the perfusate outflow cannula 30 was immediately linked to tube 82 with luer lock fitting 33 (ISIS), and connected to the perfusion circuit. Then, the perfusate inflow cannula 20 was immediately cut off from the preperfusion circuit with luer lock fitting 23 (ISIS), and by linking the perfusate inflow cannula 20 and tube 80 via luer lock fitting 23 (ISIS), sterilely connected to the perfusion circuit prefilled with culture solution and bubbles removed to prevent entrainment of bubbles into the liver. Further, the liquid flow of the perfusion circuit was simultaneously started by removing the Pean hemostatic forceps (Natume) of the perfusion circuit.

The liver 100 was mounted on a platform in the culture vessel 10.

3-2. Stationary Fixation in Solution (Conventional Method)

The liver 100 was connected to the perfusion circuit with a method similar to 3-1.

The liver 100 was mounted on the platform in the culture vessel 10, covered with gauze so that the liver does not float up due to buoyancy when the culture vessel 10 is filled with liquid, leaving enough space so as to avoid compression, and the gauze was fixed to the platform.

Then, the culture vessel 10 was filled with PBS (−) allowing the liver to lightly float and the vessel was sealed.

3-3. Hanging Fixation (Method of Present Application)

The liver 100 was connected to the perfusion circuit with a method similar to 3-1.

As shown in FIG. 2, after the ribs 104 were fixed in several places to the fixture 108 attached to the culture vessel 10 with silk suture No. 4 (Natume) 106, the culture vessel 10 was sealed, the culture vessel was placed vertically so that the inflow cannula 20 will be placed on the lower side, and the liver 100 was hanged by the ribs 104 and the diaphragm 102.

3-4. Hanging Fixation in Solution (Method of Present Application)

The liver 100 was connected to the perfusion circuit with a method similar to 3-1.

After the ribs 104 were fixed in several places to the fixture 108 attached to the culture vessel 10 with silk suture No. 4 (Natume) 106, the culture vessel 10 was filled with PBS (−) to allow the liver to float. The culture vessel was sealed, the culture vessel 10 was placed vertically so that the inflow cannula 20 will be placed on the lower side, and the liver 100 was hanged by the ribs 104 and the diaphragm 102 and floated.

4. Liver Perfusion Culture

The peristaltic pump 70 (IWAKI) between the perfusate inflow cannula 20 and the microcarrier spinner flask 62 (Bellco) was adjusted to a flow rate of 10 ml/min, and the perfusate was allowed to flow into the liver 100.

The altitude of the culture vessel was adjusted so that the outflow rate will be 10 ml/min by gravity due to difference of elevation by raising and holding the culture vessel higher in the vertical direction than the spinner flask 62. Adjustment of these flow rates was performed with the perfusate amount recovered from the perfusate recovery tube in a certain period of time. Moreover, the peristaltic pump 72 between the 100 ml Scott bottle 60 (DURAN) and the microcarrier spinner flask 62 (IWAKI) was also adjusted to have a flow rate of 10 ml/min. In addition, aeration filters (Millipore) were installed on the lids of the Scott bottle 60 and the microcarrier spinner flask 62 so that the pressure inside the circuit will not be changed by the peristaltic pump 72.

5. Verification of Circulation of Perfusate to Blood Vessels in Organ

Figure 6:
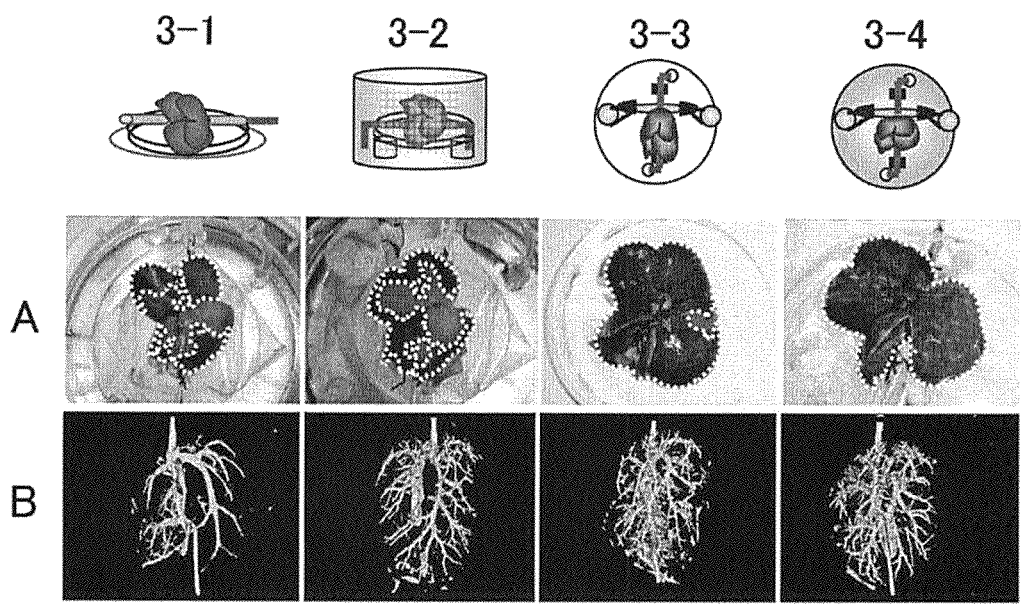
FIG. 6 is the appearance and micro-CT images after circulating trypan blue in a liver subjected to perfusion culture by various fixation methods.

For livers fixed with each fixation method described in 3-1 to 3-4, appearance and micro-CT images of the livers were photographed after pumping 10 ml of trypan blue solution (Sigma) diluted 5-fold with PBS (−) according to the method of "4. Liver Perfusion Culture". The result is shown in FIG. 6. In FIG. 6, 3-1 shows the conventional stationary fixation, 3-2 shows stationary fixation in liquid, 3-3 shows hanging fixation, and 3-4 shows hanging fixation in liquid. In FIG. 6, A is the photograph showing the appearance of the liver, and B shows the micro-CT image of the liver. In the photographs showing appearance, the area enclosed in dotted line is the portion stained by trypan blue.

For the conventional stationary fixation (3-1) and stationary fixation in liquid (3-2), not the entire organ was stained blue, and no staining was observed in the area where each lobe of the liver is folded over one another. For hanging fixation (3-3), although a portion where no staining was observed existed, nearly all parts of the organ was stained, and it became clear that the circulation of the perfusate within the organ had improved compared to the conventional stationary fixation or stationary fixation in liquid. For hanging fixation in liquid (3-4), it was shown that circulation was further improved than hanging fixation and the perfusate was circulated to all blood vessels in the organ since the entire organ was evenly stained blue.

6. Measurement of Perfusion Rate

For livers fixed with the fixation methods described in 3-1 and 3-4 and perfusion cultured for 24 hours, the perfusate was collected for 30 seconds into a 15 ml tube (BD) connected to the flow path switch cock every one hour, and the flow rate of the perfusate flowing into the liver and the flow rate of the perfusate flowing out of the liver were measured. The percentage of the outflow amount relative to the inflow amount was calculated as the perfusion rate.

A perfusion rate of 90% or higher was maintained for 24 hours in all cases, confirming that normal perfusion culture was being carried out.

7. Measurement of Impaired Enzyme Activity

The perfusate was recovered for 30 seconds in a 15 ml tube (BD) connected to the flow path switch cock every one hour, the recovered perfusate was aliquoted in 50 μl portions into 0.5 ml tubes (Eppendorf, Hamburg, Germany), and cryopreserved at −80° C. At a later date, the cryopreserved perfusate was thawed, centrifuged at 15000 rpm for 5 minutes, and GOT and GPT enzyme activity of the supernatant thereof were measured according to the method attached to Transaminase CII-Test Wako (Wako). The measurements after exchanging the perfusate were calculated by adding on the measurement value that changed before and after the exchange.

Figure 7:
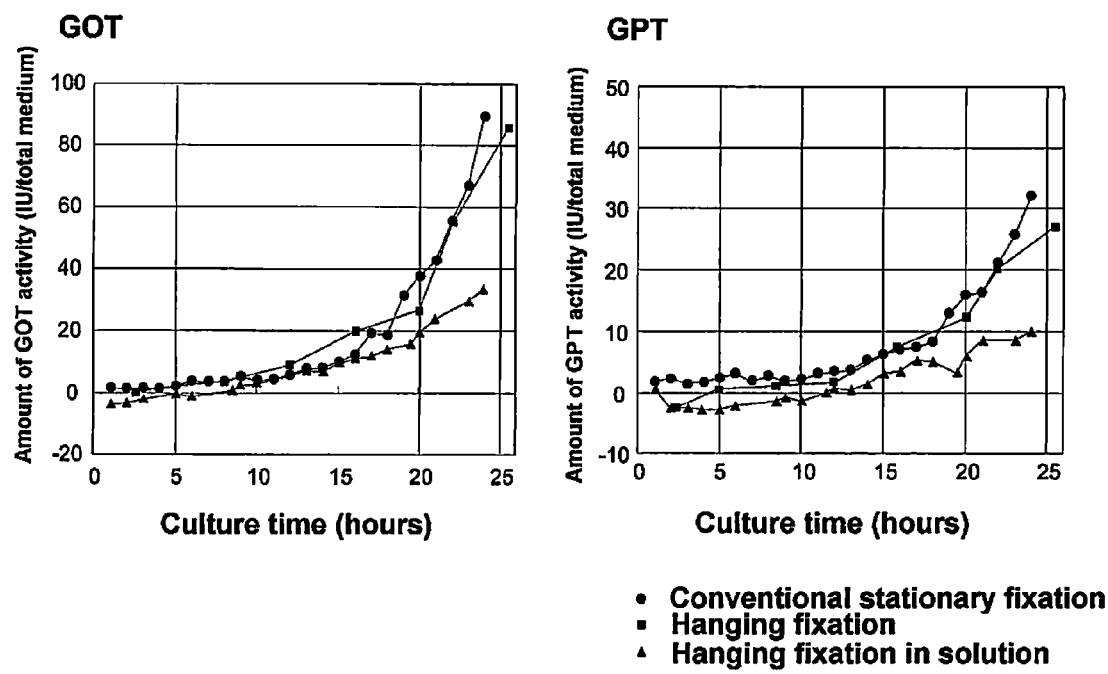
FIG. 7 is the change over time of GOT and GPT in a liver subjected to perfusion culture by various fixation methods.

The measurement result is shown in FIG. 7. For each of the conventional stationary fixation, hanging fixation, and hanging fixation in solution, GOT was 20 IU or less/total medium and GPT was 10 IU or less/total medium up to 18 hours of perfusion culture.

For the conventional stationary fixation (3-1) after 24 hours of culture, GOT was 85 IU or more/total medium and GPT was 30 IU or more/total medium, and for hanging fixation (3-3), GOT was 70 IU or more/total medium and GPT was 25 IU or more/total medium. On the other hand, for hanging fixation in solution (3-4) after 24 hours of culture, GOT was 40 IU or less/total medium and GPT was 10 IU or less/total medium. Accordingly, it became clear that in hanging fixation in solution where circulation to all blood vessels in the organ is ensured, impairing of organ is suppressed compared to the conventional stationary fixation or hanging fixation.

8. Measurement of Amount of Urea Synthesis

The perfusate was recovered for 30 seconds in a 15 ml tube (BD) connected to the flow path switch cock 84 every one hour, and the recovered perfusate was aliquoted in 1 ml portions into 1.5 ml tubes (Eppendorf, Hamburg, Germany), and cryopreserved at −80° C. At a later date, the cryopreserved perfusate was thawed, centrifuged at 15000 rpm for 5 minutes, and urea was measured according to the method attached to F-kit (J.K International). The measurements after exchanging the perfusate were calculated by adding on the measurement value that changed before and after the exchange.

Figure 8:
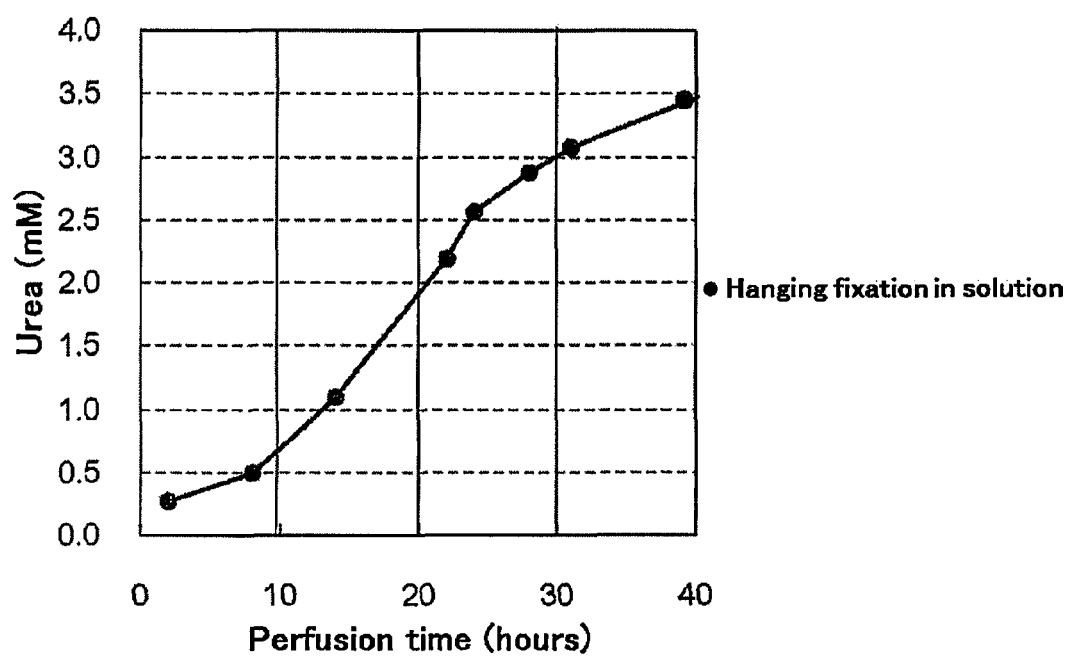
FIG. 8 is the change over time of the amount of urea synthesis in a liver subjected to perfusion culture by the hanging fixation method in liquid.

The measurement result is shown in FIG. 8. For hanging fixation in solution, the measurements were 1.098 mM up to 14 hours of perfusion culture, 2.566 mM at 24 hours of culture, and 3.529 mM at 41.5 hours of culture.

Accordingly, it became clear that in hanging fixation in solution where circulation to all blood vessels in the organ is ensured, urea synthesis capability is maintained beyond the liver preservation limit of the conventional method which is 20 hours.

9. Measurement of Amount of Bile secretion

For the amount of bile recovered into the bile recovery circuit (tube 88 and Scott bottle 68), the amount of bile secretion was measured with an electronic balance from the weight recovered every one hour.

Figure 9:
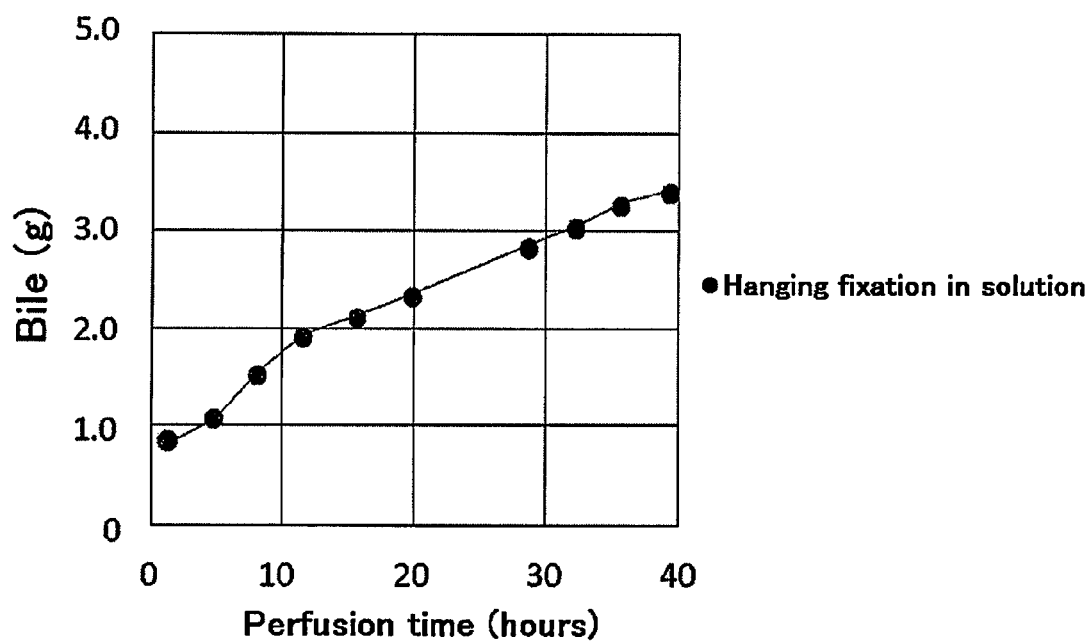
FIG. 9 is the change over time of the amount of bile secretion in a liver subjected to perfusion culture by the hanging fixation method in liquid.

The measurement result is shown in FIG. 9. For hanging fixation in solution, chronological bile secretion of 0.06 g per hour from the beginning of perfusion culture to 40 hours of culture was verified.

Accordingly, it became clear that in hanging fixation in solution where circulation to all blood vessels in the organ is ensured, bile productivity is maintained beyond the liver preservation limit of the conventional method which is 20 hours.

10. Removal of Kidney and Connection to Preperfusion Circuit

The kidney was removed from a rat, and connected to the preperfusion circuit shown in FIG. 5 instead of the liver via perfusate inflow/outflow cannula 20 and 30 employed for kidney perfusion culture.

A desiccator was filled with diethyl ether (Wako), an 8-10 week-old Wistar rat (SLC) was transferred to the desiccator for inhalation anesthesia, and then 400 μl of pentobarbital sodium (TCI, Tokyo, Japan) solution at a final concentration of 25 mg/ml was intraperitoneally injected with an 25G injection needle (Terumo) and a 1 ml syringe (Terumo).

Incision was made to the skin of a rat under deep anesthesia from lower abdomen to below the throat along the midline. The peritoneum was incised, and the organs of the digestive system were moved to expose the kidney, the renal artery, the renal vein, and the urinary duct. The renal artery, renal vein, and urinary duct were detached from the surrounding tissue, silk sutures No. 4 (Natume) were pulled through from under each of the renal artery, renal vein, and urinary duct, and two ligature loops were created for each. The perfusate was flowed through the preperfusion circuit (FIG. 5) in advance at 0.2 ml/min, the renal artery was bisected at a site away from the kidney than the two renal artery ligature loops, and the perfusate inflow cannula 20 was quickly inserted into the renal artery. The dorsal vena cava was immediately cut to allow inflow of the perfusate.

The two renal artery ligature loops were ligated to fix the perfusate inflow cannula 20 to the renal artery, the renal vein was bisected, and the perfusate outflow cannula 30 was quickly inserted into the renal vein. The two renal vein ligature loops were ligated to fix the perfusate outflow cannula 30 to the renal vein, and the cannulation portion was fixed with a small amount of Aron Alpha A (Daiichi Sankyo, Tokyo, Japan). The urinary duct was bisected and the ureteral cannula 40 was inserted, the loop was ligated, and then fixed with Aron Alpha A (Daiichi Sankyo).

In order to remove the kidney, after excising other organs, the kidney was cut away from the backside with adipose tissue surrounding the kidney still attached to the kidney.

11. Connection to Kidney Perfusion Circuit 11-1. Stationary Fixation (Conventional Method)

First, while the kidney is still connected to the preperfusion circuit, the perfusate inflow cannula 20 was fixed to the fixture 96 of the culture vessel 10, the perfusate outflow cannula 30 was fixed to the fixture 98, and the ureteral cannula 40 was also fixed to a fixture (not shown). The ureteral cannula 40 was connected via luer lock fitting 43 (ISIS) to the urine recovery circuit that flows to the outside of the culture vessel 10 (tube 88 and Scott bottle 68).

Next, the silicone tube (ASONE) connected to the perfusate inflow cannula 20 was clipped with Pean hemostatic forceps (Natume) to temporarily stop the liquid flow, and then the perfusate outflow cannula 30 was immediately linked to tube 82 with luer lock fitting 33 (ISIS), and connected to the perfusion circuit. Then, the perfusate inflow cannula 20 was immediately cut off from the preperfusion circuit with luer lock fitting 23 (ISIS), and by linking the perfusate inflow cannula 20 and tube 80 via luer lock fitting 23 (ISIS), sterilely connected to the perfusion circuit prefilled with culture solution and bubbles removed to prevent entrainment of bubbles into the kidney. Further, the liquid flow of the perfusion circuit was simultaneously started by removing the Pean hemostatic forceps (Natume) of the perfusion circuit.

The kidney was mounted on a platform in the culture vessel 10.

11-2. Hanging Fixation in Solution (Method of Present Application)

First, with the kidney still connected to the preperfusion circuit, the kidney along with the renal artery, renal vein, and urinary duct were moved onto silicone rubber while maintaining the positional relationship with the kidney, and the perfusate inflow/outflow/ureteral cannula 20, 30, and 40 were fixed to the silicone rubber with 25G injection needles (Terumo). Each cannula was fixed by crossing and piercing two injection needles so that they straddle each cannula as if to press them down. Further, the adipose tissue surrounding the kidney was fixed to the silicone rubber with 25G injection needles (Terumo).

The perfusate inflow cannula 20 was fixed to the fixture 96 of the culture vessel 10, the perfusate outflow cannula 30 was fixed to the fixture 98, and the ureteral cannula 40 was also fixed to a fixture (not shown). The ureteral cannula 40 was connected via luer lock fitting 43 (ISIS) to the urine recovery circuit (tube 88 and Scott bottle 68) that flows to the outside of the culture vessel 10.

Next, the silicone tube (ASONE) connected to the perfusate inflow cannula 20 was clipped with Pean hemostatic forceps (Natume) to temporarily stop the liquid flow, and then the perfusate outflow cannula 30 was immediately linked to tube 82 with luer lock fitting 33 (ISIS), and connected to the perfusion circuit. Then, the perfusate inflow cannula 20 was immediately cut off from the preperfusion circuit with luer lock fitting 23 (ISIS), and by linking the perfusate inflow cannula 20 and tube 80 via luer lock fitting 23 (ISIS), sterilely connected to the perfusion circuit prefilled with culture solution and bubbles removed to prevent entrainment of bubbles into the liver. Further, the liquid flow of the perfusion circuit was simultaneously started by removing the Pean hemostatic forceps (Natume) clipped beforehand.

After inverting the silicone rubber to which the kidney is fixed and hanging the kidney, and fixing the silicone rubber to the fixture 108 attached to the culture vessel 10 with silk suture No. 4 (Natume) 106, the culture vessel 10 was filled with PBS (−) to allow the kidney to float. The culture vessel was sealed, the culture vessel 10 was placed vertically so that the inflow cannula will be placed on the lower side, and the kidney was hanged and floated by the surrounding adipose tissue.

12. Kidney Perfusion Culture

The peristaltic pump 70 (IWAKI) between the perfusate inflow cannula 20 and the microcarrier spinner flask 62 (Bellco) was appropriately adjusted so that the urine amount will be 0.3 ml/hour, and the perfusate was allowed to flow into the kidney.

The perfusate was allowed to flow out of the kidney by gravity due to difference of elevation by raising and holding the culture vessel higher in the vertical direction than the spinner flask 62. Other conditions were similar to that for liver perfusion culture.

13. Measurement of Impaired Enzyme Activity

The urine recovered into the urine recovery circuit (tube 88 and Scott bottle 68) was aliquoted in 50 µl portions into 0.5 ml tubes (Eppendorf, Hamburg, Germany), and cryopreserved at −80° C. At a later date, the cryopreserved urine was thawed, centrifugated at 15000 rpm for 5 minutes, and GOT/GPT enzyme activity of the supernatant thereof were measured according to the method attached to Transaminase CII-Test Wako (Wako).

Figure 10:
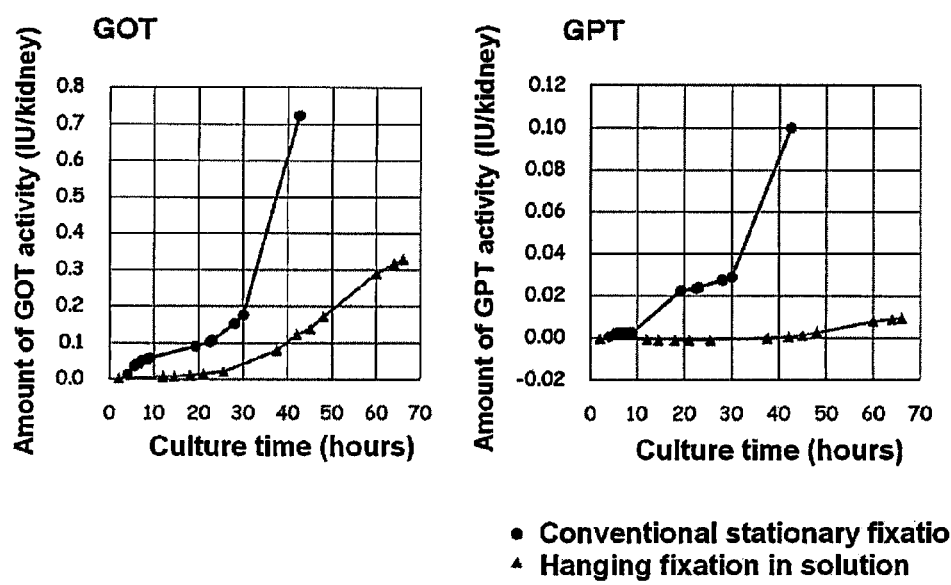
FIG. 10 is the change over time of GOT and GPT in a kidney subjected to perfusion culture by the stationary fixation method and the hanging fixation method in liquid.

The measurement result is shown in FIG. 10. For the conventional stationary fixation (11-1) after 40 hours of culture, GOT was 0.6 IU/kidney or more and GPT was 0.08 IU/kidney or more, whereas for hanging fixation in solution (11-2), GOT was about 0.1 IU/kidney and GPT was nearly 0 IU/kidney. Further, for hanging fixation in solution (11-2) after 60 hours of culture, GOT was about 0.3 IU/Kidney and GPT was about 0.01 IU/Kidney. Accordingly, it became clear that impairing of organ is suppressed for hanging fixation in solution compared to the conventional stationary fixation.

DESCRIPTION OF SYMBOLS

1: organ perfusion culture device; 10: culture vessel; 20: perfusate inflow cannula; 21, 31, 41, 109, 110, 111: liver/kidney catheter part; 22, 32, 42: Parafilm; 23, 33, 43: Parafilm; 24, 34: flexible silk suture; 25, 35, 45: silicone tube; 30: perfusate outflow cannula; 40: biliary/ureteral cannula; 50, 50': bubble removal device; 60, 64, 66, 68, 92: Scott bottle; 62: microcarrier spinner flask; 70, 72, 74, 78, 94: pump; 80, 82, 88: tube; 84, 86: flow path switch cock; 96, 98: fixture; 99a, 99b: through-hole; 100: liver; 102: diaphragm; 104: rib; 106: suture, and 108: fixture.

The invention claimed is:

1. A method for perfusion culture of an organ or tissue removed from a mammal, wherein said organ or tissue is removed together with a second organ or tissue which is connected to the organ or tissue in vivo, wherein the second tissue or organ is not a blood vessel, comprising: hanging the organ or tissue by fixing the second organ or tissue, and perfusing the blood vessels in the organ or tissue with a perfusate.

2. The perfusion culture method according to claim 1, wherein in the said perfusion step, at least a part of the organ or tissue is immersed in a liquid.

3. The perfusion culture method according to claim 2, wherein the organ or tissue is a liver, and the second organ or tissue is a diaphragm.

4. The perfusion culture method according to claim 2, wherein the organ or tissue is a liver, and the second organ or tissue a diaphragm and a rib.

5. The perfusion culture method according to claim 2, wherein the organ or tissue is a kidney, and the second organ or tissue is adipose tissue surrounding the kidney, wherein the adipose tissue is connected to the kidney.

6. The perfusion culture method according to claim 1, wherein the organ or tissue is a liver, and the second organ or tissue is a diaphragm.

7. The perfusion culture method according to claim 1, wherein the organ or tissue is a liver, and the second organ or tissue is a diaphragm and a rib.

8. The perfusion culture method according to claim 1, wherein the organ or tissue is a kidney, and the second organ or tissue is adipose tissue surrounding the kidney, wherein the adipose tissue is connected to the kidney.

* * * * *